US012016755B2

(12) United States Patent
Bairstow (10) Patent No.: US 12,016,755 B2
(45) Date of Patent: Jun. 25, 2024

(54) TAMPON

(71) Applicant: John Anthony Bairstow, Leeds (GB)

(72) Inventor: John Anthony Bairstow, Leeds (GB)

(73) Assignee: John Anthony Bairstow, Leeds (GB)

( * ) Notice: Subject to any disclaimer, the term of this patent is extended or adjusted under 35 U.S.C. 154(b) by 576 days.

(21) Appl. No.: 17/422,585

(22) PCT Filed: Jan. 15, 2020

(86) PCT No.: PCT/GB2020/050082
§ 371 (c)(1),
(2) Date: Jul. 13, 2021

(87) PCT Pub. No.: WO2020/148537
PCT Pub. Date: Jul. 23, 2020

(65) Prior Publication Data
US 2022/0087875 A1 Mar. 24, 2022

(30) Foreign Application Priority Data
Jan. 18, 2019 (GB) ...................................... 1900729

(51) Int. Cl.
*A61F 13/20* (2006.01)
*A61F 13/26* (2006.01)
*A61F 13/34* (2006.01)

(52) U.S. Cl.
CPC ...... *A61F 13/2042* (2013.01); *A61F 13/2025* (2013.01); *A61F 13/2051* (2013.01);
(Continued)

(58) Field of Classification Search
CPC .............. A61F 13/2042; A61F 13/2025; A61F 13/2051; A61F 13/2068; A61F 13/2071
See application file for complete search history.

(56) References Cited

U.S. PATENT DOCUMENTS 4,278,088 A * 7/1981 Reeves .................. A61L 15/60
604/15
4,887,597 A * 12/1989 Holland .................... A61F 5/08
128/206.11
(Continued)

FOREIGN PATENT DOCUMENTS

CA 1123155 A 5/1982
WO WO-2010114444 A1 * 10/2010 ......... A61F 13/2051

OTHER PUBLICATIONS

International Search Report (ISR) for PCT/GB2020/050082 mailed on Apr. 8, 2020 (4 pages).
(Continued)

*Primary Examiner* — Susan S Su
(74) *Attorney, Agent, or Firm* — Shumaker, Loop & Kendrick, LLP (57) ABSTRACT

A tampon including a body having a longitudinal axis, a front end, a rear end and an outer surface. The body including a liquid-absorbing material operable to absorb and/or retain bodily fluid. A bore extending through the body along the longitudinal axis from the front end to the rear end, said bore defining an inner surface. The tampon also including a liquid-impermeable layer, which includes a liquid-impermeable elastic material and a liquid-permeable layer. The liquid-absorbing material is a fluid. One of the liquid-impermeable layer or the liquid-permeable layer is on at least a portion of the outer surface of the body of the tampon. The other of the liquid-impermeable layer or the liquid-permeable layer is on at least a portion of the inner surface of the body. In use, the liquid-impermeable layer and the liquid-permeable layers are operable to move between a first configuration and a second configuration.

18 Claims, 3 Drawing Sheets

(52) U.S. Cl.
    CPC ...... *A61F 13/2068* (2013.01); *A61F 13/2071* (2013.01); *A61F 13/266* (2013.01); *A61F 13/34* (2013.01)

(56) References Cited

U.S. PATENT DOCUMENTS

| | | | |
|---|---|---|---|
| 5,476,455 A * | 12/1995 | Silber | A61F 13/34 604/330 |
| 2002/0142693 A1 | 10/2002 | Buzot | |
| 2006/0025740 A1 | 2/2006 | Osborn, III et al. | |

OTHER PUBLICATIONS

Written Opinion for PCT/GB2020/050082 mailed on Apr. 8, 2020 (6 pages).

* cited by examiner

TAMPON

FIELD

The present invention relates to a tampon, in particular to an intravaginal tampon, even more particularly to an intravaginal tampon operable to absorb and/or retain menstrual fluid.

BACKGROUND

Feminine hygiene devices for absorbing, capturing and/or retaining bodily fluids, such as menstrual fluids are known. Known feminine hygiene devices may be used either externally, in the form of a sanitary pad, for example, or intravaginally. Common devices for intravaginally absorbing, and retaining bodily fluid, such as menstrual fluid, are intravaginal tampons. Typically, tampons have a cylindrical form and are made from compressed absorbent fibres which may optionally be contained in an absorbent or non-absorbent outer layer.

In use, tampons are inserted into the human vagina and are retained in the vagina for a period of time. During this time the absorbent fibres of the tampon absorb and retain bodily fluid, such as menstrual fluid. After said period of time, the tampon and the fluid which it has absorbed and retained is removed and disposed of. Another tampon may then be inserted into the vagina if necessary.

However, there are drawbacks with known tampons. For example, known tampons can typically not be used, or are uncomfortable to use, at the very beginning of the period due to a lack of lubrication which can make insertion uncomfortable and/or difficult. Further, known tampons can be uncomfortable to insert and/or remove at any time during the period due to, for example, the materials from which known tampons are made and/or the methods by which they are inserted and/or removed.

Known tampons can cause infections, such as toxic shock syndrome (TSS), if they are retained in the vagina for too long. TSS is caused by staphylococcal and/or streptococcal bacteria, each of which requires oxygen. Although known tampons are formed from compressed fibres, air is still present in these devices and, therefore, the risk of infection from bacteria such as staphylococcal and/or streptococcal bacteria can not be eliminated.

Known tampons can also have problems relating to hygienic handling. For example, when known tampons are removed after use, the absorbed and retained menstrual fluid may be exposed on the outer surface of the tampon during and after removal.

It is an object of aspects of the present invention to provide one or more solutions to one of the above mentioned or other problems.

SUMMARY

According to a first aspect of the present invention there is provided a tampon, the tampon comprising:
- a body having a longitudinal axis, a front end, a rear end and an outer surface, said body comprising a liquid-absorbing material operable to absorb and/or retain bodily fluid;
- a bore extending through the body along the longitudinal axis from the front end to the rear end, said bore defining an inner surface;
- a liquid-impermeable layer, said liquid-impermeable layer comprising a liquid-impermeable elastic material; and
- a liquid-permeable layer;
- wherein the liquid-absorbing material is a fluid;
- wherein one of the liquid-impermeable layer or the liquid-permeable layer is on at least a portion of the outer surface of the body of the tampon and the other of the liquid-impermeable layer or the liquid-permeable layer is on at least a portion of the inner surface of the body;
- and wherein, in use, the liquid-impermeable layer and the liquid-permeable layers are operable to move between a first configuration and a second configuration.

The present invention is a tampon. For the avoidance of doubt, by "tampon", and like terms as used herein, is meant a device that can be used to plug a wound and/or an opening in the body, such as, for example, the vagina, and is suitable to absorb bodily fluid, such as menstrual fluid, blood or secretions.

Suitably, the tampon may be an intravaginal tampon. Suitably, the tampon may be an intravaginal tampon operable to absorb and/or retain menstrual fluid.

Advantageously, the tampon of the present invention may be caused to 'self-insert' when a compressive force is applied to the front end and/or the rear end of the body of the tampon. By 'self-insert' and like terms as used herein, is meant that the tampon is operable to move axially along the longitudinal axis when a compressive force is applied to the front end and/or rear end of the body of the tampon without the need to apply a further force to the tampon, such as a further pushing and/or pulling force, for example. The compressive force may be applied by a user, may be applied as a result of the elastic nature of the liquid-impermeable layer and/or may be applied as a result of the elastic nature of one or more other components of the tampon.

One of the liquid-impermeable layer or the liquid-permeable layer is on at least a portion of the outer surface of the body of the tampon and the other of the liquid-impermeable layer or the liquid-permeable layer is on at least a portion of the inner surface of the body.

Suitably, the liquid-impermeable layer may be on at least a portion of the outer surface of the body of the tampon prior to insertion into an opening in the body, such as, for example, the vagina. Suitably, the liquid-impermeable layer may be on at least a portion of the inner surface of the body of the tampon after insertion into an opening in the body, such as, for example, the vagina.

Suitably, the liquid-permeable layer may be on at least a portion of the inner surface of the body of the tampon prior to insertion into an opening in the body, such as, for example, the vagina. Suitably, the liquid-permeable layer may be on at least a portion of the outer surface of the body of the tampon after insertion into an opening in the body, such as, for example, the vagina.

The liquid-impermeable layer and the liquid-permeable layers are operable to move between a first configuration and a second configuration. Suitably, the first configuration may be the configuration prior to insertion of the tampon into an opening in the body, such as, for example, the vagina. Suitably, the second configuration may be the configuration after insertion of the tampon into an opening of the body, such as, for example, the vagina. It will be understood by a person skilled in the art that "after insertion", and like terms as used herein, means the configuration once the tampon has been fully inserted into an opening of the body, such as, for example, the vagina, to the required distance. For the avoidance of doubt, reference herein to 'a/the first configuration' and 'a/the configuration prior to insertion of the tampon into an opening in the body, such as, for example, the vagina' may be used interchangeably. For the avoidance of doubt, reference herein to 'a/the second configuration' and 'a/the configuration after insertion of the tampon into an opening in the body, such as, for example, the vagina' may be used interchangeably.

The first configuration may be any suitable configuration. Suitably, the liquid-impermeable layer may be on at least a portion of the outer surface of the body of the tampon and the liquid-permeable layer may be on at least a portion of the inner surface of the body of the tampon in the first configuration.

The second configuration may be any suitable configuration. Suitably, the liquid-permeable layer may be on at least a portion of the outer surface of the body of the tampon and the liquid-impermeable layer may be on at least a portion of the inner surface of the body of the tampon in the second configuration.

Without being bound by theory, the fluid nature of the liquid-absorbing material of the body of the tampon and the elastic nature of the liquid-impermeable elastic material of the liquid-impermeable layer are such that, when a compressive force is applied to the front end and/or the rear end of the body of the tampon, the liquid-absorbing material is caused to move axially along the longitudinal axis. When the liquid-absorbing material is caused to move axially along the longitudinal axis, the layer on at least a portion of the outer surface of the body of the tampon is caused to move inwards into the bore such that said layer becomes located on at least a portion of the inner surface of the body of the tampon. When the liquid-absorbing material is caused to move axially along the longitudinal axis, the layer on at least a portion of the inner surface of the body of the tampon is caused to move outwards from the bore to the outer surface of the body of the tampon such that said layer becomes located on at least a portion of the outer surface of the body of the tampon. In other words, when the liquid-absorbing material is caused to move axially along the longitudinal axis, the liquid-permeable layer of the tampon and the liquid-impermeable layer the tampon may be caused to become reversed.

Suitably, therefore, the liquid-impermeable layer and the liquid-permeable layer may together form a reversible sleeve. Suitably, the reversible sleeve may be caused to become reversed during use of the tampon.

By "reversible sleeve", and like terms as used herein, is meant that the liquid-impermeable layer and liquid-permeable layer are attached so as to form a continuous sleeve and that the respective positions of the liquid-permeable layer and the liquid-impermeable layer may become reversed, for example, during use. It is an advantage of the present invention that the tampon may 'self-insert' because, for example, this means that the tampon may be more comfortable to insert than would typically be expected and/or may be more hygienically inserted than would typically be expected. It is a further advantage of the present invention that the tampon may be removed more comfortably than would typically be expected and/or may be more hygienically removed than would typically be expected. It is an advantage of the present invention that, in use, the liquid-permeable layer may be disposed on at least a portion of the outer surface of the body of the tampon when the tampon is inserted into the body, for example, into the vagina. In this way, in use, the liquid-permeable layer may allow bodily fluid, such as menstrual fluid, to pass through said liquid-permeable layer such that it may be absorbed and/or retained by the liquid-absorbing material of the body of the tampon.

Suitably, the tampon may be operable to move forward along the longitudinal axis when a compressive force is applied to the rear end of the body. By "forward along the longitudinal axis", and like terms as used herein, is meant that the tampon is operable to move along the longitudinal axis in the direction extending from the rear end of the body to the front end of the body.

Suitably, the tampon may be operable to move backward along the longitudinal axis when a compressive force is applied to the front end of the body. By "backward along the longitudinal axis", and like terms as used herein, is meant that the tampon is operable to move along the longitudinal axis in the direction extending from the front end of the body to the rear end of the body.

The tampon comprises a body. The body may be any suitable shape. Suitably, the body may be substantially cylindrical in shape.

The body may have any suitable length. The body may have a length of at least 20 millimetres (mm), suitably at least 25 mm, such as at least 30 mm, such as at least 35 mm, such as at least 40 mm, such as at least 45 mm, such as at least 50 mm, or even at least 55 mm. The body may have a length of up to 120 mm, such as up to 110 mm, such as 100 mm, such as up to 95 mm, such as up to 90 mm, such as up to 85 mm, such as up to 80 mm, such as up to 75 mm, such as up to 70 mm, such as up to 65 mm, or even up to 60 mm.

The body may have a length from 20 to 120 mm, such as from 20 to 110 mm, such as from 20 to 100 mm, such as from 20 to 95 mm, such as from 20 to 90 mm, such as from 20 to 85 mm, such as from 20 to 80 mm, such as from 20 to 75 mm, such as from 20 to 70 mm, such as from 20 to 65 mm, or even from 20 to 60 mm. The body may have a length from 25 to 120 mm, such as from 25 to 110 mm, such as from 25 to 100 mm, such as from 25 to 95 mm, such as from 25 to 90 mm, such as from 25 to 85 mm, such as from 25 to 80 mm, such as from 25 to 75 mm, such as from 25 to 70 mm, such as from 25 to 65 mm, or even from 25 to 60 mm. The body may have a length from 30 to 120 mm, such as from 30 to 110 mm, such as from 30 to 100 mm, such as from 30 to 95 mm, such as from 30 to 90 mm, such as from 30 to 85 mm, such as from 30 to 80 mm, such as from 30 to 75 mm, such as from 30 to 70 mm, such as from 30 to 65 mm, or even from 30 to 60 mm. The body may have a length from 35 to 120 mm, such as from 35 to 110 mm, such as from 35 to 100 mm, such as from 35 to 95 mm, such as from 35 to 90 mm, such as from 35 to 85 mm, such as from 35 to 80 mm, such as from 35 to 75 mm, such as from 35 to 70 mm, such as from 35 to 65 mm, or even from 35 to 60 mm. The body may have a length from 40 to 120 mm, such as from 40 to 110 mm, such as from 40 to 100 mm, such as from 40 to 95 mm, such as from 40 to 90 mm, such as from 40 to 85 mm, such as from 40 to 80 mm, such as from 40 to 75 mm, such as from 40 to 70 mm, such as from 40 to 65 mm, or even from 40 to 60 mm. The body may have a length from 45 to 120 mm, such as from 45 to 110 mm, such as from 45 to 100 mm, such as from 45 to 95 mm, such as from 45 to 90 mm, such as from 45 to 85 mm, such as from 45 to 80 mm, such as from 45 to 75 mm, such as from 45 to 70 mm, such as from 45 to 65 mm, or even from 45 to 60 mm. The body may have a length from 50 to 120 mm, such as from 50 to 110 mm, such as from 50 to 100 mm, such as from 50 to 95 mm, such as from 50 to 90 mm, such as from 50 to 85 mm, such as from 50 to 80 mm, such as from 50 to 75 mm, such as from 50 to 70 mm, such as from 50 to 65 mm, or even from 50 to 60 mm. The body may have a length from 55 to 120 mm, such as from 55 to 110 mm, such as from 55 to 100 mm, such as from 55 to 95 mm, such as from 55 to 90 mm, such as from 55 to 85 mm, such as from 55 to 80 mm, such as from 55 to 75 mm, such as from 55 to 70 mm, such as from 55 to 65 mm, or even from 55 to 60 mm.

Suitably, the body may have a length from 55 to 65 mm. More suitably, the body may have a length from 55 to 60 mm.

For the avoidance of doubt, the term "length" as used herein with reference to the body, unless specified otherwise, refers to the dimension along the longitudinal axis.

The body may have any suitable width. The body may have a width of at least 5 mm, such as at least 7 mm, such as at least 10 mm, or even at least 12 mm. The body may have a width of up to 45 mm, such as up to 40 mm, such as up to 35 mm, 30 mm, such as up to 25 mm, such as up to 20 mm, such as up to 17 mm, or even up to 15 mm.

The body may have a width from 5 to 45 mm, such as from 7 to 45 mm, such as from 10 to 45 mm, or even from 12 to 45 mm. The body may have a width from 5 to 40 mm, such as from 7 to 40 mm, such as from 10 to 40 mm, or even from 12 to 40 mm. The body may have a width from 5 to 35 mm, such as from 7 to 35 mm, such as from 10 to 35 mm, or even from 12 to 35 mm. The body may have a width from 5 to 30 mm, such as from 7 to 30 mm, such as from 10 to 30 mm, or even from 12 to 30 mm. The body may have a width from 5 to 25 mm, such as from 7 to 25 mm, such as from 10 to 25 mm, or even from 12 to 25 mm. The body may have a width from 5 to 20 mm, such as from 7 to 20 mm, such as from 10 to 20 mm, or even from 12 to 20 mm. The body may have a width from 5 to 17 mm, such as from 7 to 17 mm, such as from 10 to 17 mm, or even from 12 to 17 mm. The body may have a width from 5 to 15 mm, such as from 7 to 15 mm, such as from 10 to 15 mm, or even from 12 to 15 mm.

Suitably, the body may have a width from 10 to 20 mm. More suitably, the body may have a width from 12 to 17 mm. Even more suitably, the body may have a width from 12 to 15 mm.

For the avoidance of doubt, the term "width" as used herein with reference to the body, unless specified otherwise, refers to the dimension perpendicular, i.e. lateral, to the longitudinal axis. It will be appreciated by a person skilled in the art that when the body is substantially cylindrical in shape, the width will be equivalent to the diameter of the cylinder.

For the avoidance of doubt, reference to "length" and/or "width" as used herein with reference to the body, unless specified otherwise, refers to the dimensions of the tampon when external to the body and prior to the tampon being inserted into the body.

The body has a longitudinal axis. For the avoidance of doubt, by "longitudinal axis", and like terms as used herein, is meant that the axis runs along the length of the body of the tampon. The body, in having a longitudinal axis, may suitably be elongated. The longitudinal axis may run substantially centrally though the body of the tampon or may be offset from central. Suitably, the longitudinal axis may run centrally though the body of the tampon.

The body has a front end. By "front end", and like terms as used herein, is meant the end of the tampon which, in use, is the end that is first inserted into the body and includes up to 50% of the length of the body along the longitudinal axis. The front end may have a substantially flat shape or may be substantially dome shaped. Suitably, the front end may be substantially dome shaped. When the front end is substantially dome shaped, the dome shaped portion of the front end of the body may comprise up to 50%, such as up to 30%, such as up to 20%, such as up to 10%, such as up to 5% of the total length of the body (at the front end thereof). Suitably, when the front end is substantially dome shaped, the dome shaped portion of the front end of the body may comprise up to 10% of the total length of the body (at the front end thereof). For the avoidance of doubt, by "dome shaped portion", and like terms as used herein, is meant the portion of the length of the body (at the front end thereof) which is curved in the longitudinal direction.

The body has a rear end. By "rear end", and like terms as used herein, is meant the end of the tampon which, in use, is the end that is distal, i.e. opposite, to the end that is first inserted into the body (and is therefore inserted lastly into the body) and includes up to 50% of the length of the body along the longitudinal axis. The rear end may have a substantially flat shape or may be substantially dome shaped. Suitably, the rear end may be substantially dome shaped. When the rear end is substantially dome shaped, the dome shaped portion of the rear end of the body may comprise up to 50%, such as up to 30%, such as up to 20%, such as up to 10%, such as up to 5% of the total length of the rear end of the body (at the rear end thereof). Suitably, when the rear end is substantially dome shaped, the dome shaped portion of the rear end of the body may comprise up to 10% of the total length of the body (at the rear end thereof). For the avoidance of doubt, by "dome shaped portion", and like terms as used herein, is meant the portion of the length of the body (at the rear end thereof) which is curved in the longitudinal direction.

The body has an outer surface. For the avoidance of doubt, by "outer surface", and like terms as used herein, is meant the surface on the outside of the body of the tampon up to the opening of the bore at each of the front end and rear end of the body of the tampon and does not include the inner surface define by said bore.

The tampon comprises a liquid-impermeable layer. By "liquid-impermeable", and like terms as used herein, is meant that the liquid-impermeable layer is substantially impermeable to at least liquids. Suitably, the liquid-impermeable layer may be completely impermeable to liquids.

The liquid-impermeable layer may optionally be substantially impermeable to gases. Suitably, therefore, the liquid-impermeable layer may be substantially impermeable to fluids. The liquid-impermeable layer may optionally be completely impermeable to gases. Suitably, therefore, the liquid-impermeable layer may be completely impermeable to fluids.

Suitably, the liquid-impermeable layer may be impermeable to bodily fluids, such as menstrual fluid, and the liquid(s) of the liquid-absorbing material of the body of the tampon. Suitably, the liquid-impermeable layer may be substantially impermeable to menstrual fluid and the liquid (s) of the liquid-absorbing material of the body of the tampon. Suitably, when the liquid-absorbing material is a hydrogel, the liquid-impermeable layer may be substantially impermeable to menstrual fluid and the hydrogel.

Suitably, the liquid-impermeable layer may be completely impermeable to at least menstrual fluid and the fluid(s) of the liquid-absorbing material of the body of the tampon. Suitably, when the liquid-absorbing material is a hydrogel, the liquid-impermeable layer may be completely impermeable to at least menstrual fluid and the hydrogel.

Suitably, the liquid-impermeable layer may be on at least a portion of the outer surface of the body of the tampon in the first configuration. The liquid-impermeable layer may be disposed on any suitable area of the outer surface of the body of the tampon in the first configuration. Suitably, the liquid-impermeable layer may be disposed on at least 15%, such as at least 20%, such as at least 30%, such as at least 40%, such as at least 50% such as at least 60%, such as at least 70%, such as at least 80%, such as at least 90%, or even 100% of the area of the outer surface of the body of the tampon in the first configuration.

Suitably, the liquid-impermeable layer may be disposed on at least 80% of the area of the outer surface of the body of the tampon in the first configuration.

Suitably, the liquid-impermeable layer may be disposed on a portion of the outer surface of the body of the tampon in the first configuration.

Suitably, the liquid-impermeable layer may be disposed on from 80 to 90% of the area of the outer surface of the body of the tampon in the first configuration. More suitably, the liquid-impermeable layer may be disposed on from 85 to 90% of the area of the outer surface of the body of the tampon in the first configuration.

Advantageously, when the liquid-impermeable layer is disposed on a portion of the outer surface of the body of the tampon in the first configuration, the tampon may be operable to 'self-insert' to a distance that is longer than the length of the body of the tampon. Without being bound by theory, this may be because, in use, the liquid-impermeable layer may be caused to move axially along the outer surface of the body of the tampon and in doing so moves to either the front end or to the rear end of the body of the tampon, depending on where the initial compressive force was applied by a user, such that it is disposed on a portion of the outer surface of the body of the tampon at either the front end or the rear end of the body of the tampon. The liquid-impermeable layer therefore applies a compressive force to either the front end or the rear end of the body of the tampon, depending on where the initial compressive force was applied by a user, due to the elastic nature of the liquid-impermeable layer. This compressive force may be operable to cause the liquid-absorbing material to move axially along the longitudinal axis. For example, when the liquid-impermeable layer is disposed on a portion of the outer surface of the body of the tampon, for example in a first configuration, and when an initial compressive force is applied to the rear end of the body of the tampon by a user, the liquid-impermeable layer may be caused to move axially along the outer surface of the body of the tampon and in doing so moves to the rear end of the body of the tampon, such that it is disposed on a portion of the outer surface of the body of the tampon at the rear end of the body of the tampon. When the liquid-impermeable layer is disposed on a portion of the outer surface of the body of the tampon at the rear end of the body of the tampon, for example in a first configuration, the liquid-impermeable layer may apply a compressive force to the rear end of the body of the tampon due to the elastic nature of the liquid-impermeable layer. This compressive force may be operable to cause the liquid-absorbing material to move forward along the longitudinal axis. It will be understood by a person skilled in the art that the ability of the liquid-impermeable layer to apply a compressive force to the front end and/or rear end of the body of the tampon may depend upon the initial position of said liquid impermeable layer, for example, the portion of the outer surface on which the liquid-impermeable layer is disposed in a first configuration.

When the liquid-impermeable layer is disposed on a portion of the outer surface of the body of the tampon in the first configuration, the liquid-impermeable layer may be disposed on any suitable part of the outer surface of the body of the tampon. For example, when the liquid-impermeable layer is disposed on a portion of the outer surface of the body of the tampon in the first configuration, the liquid-impermeable layer may be disposed on a portion of the outer surface of the tampon extending from the opening of the bore at front end of the body of the tampon or a portion of the surface extending from the opening of the bore at the rear end of the body of the tampon.

Suitably, when the liquid-impermeable layer is disposed on a portion of the outer surface of the body of the tampon in a first configuration, the liquid-impermeable layer may be disposed on a portion of the outer surface of the tampon extending from the opening of the bore at front end of the body of the tampon.

When the liquid-impermeable layer is disposed on a portion of the outer surface extending from the front end of the body of the tampon in the first configuration, the liquid-impermeable layer may extend at least 15 mm, such as at least 20 mm, such as at least 25 mm, such as at least 30 mm, such as at least 35 mm, such as at least 40 mm, or even at least 45 mm along the length of the body of the tampon as measured from the front end of the body of the tampon. When the liquid-impermeable layer is disposed on a portion of the outer surface extending from the front end of the body of the tampon in the first configuration, the liquid-impermeable layer may extend up to 95 mm, such as up to 90 mm, such as up to 85 mm, such as up to 80 mm, such as up to 75 mm, such as up to 70 mm, such as up to 65 mm, such as up to 60 mm, such as up to 55 mm, or even up to 50 mm along the length of the body of the tampon as measured from the front end of the body of the tampon.

When the liquid-impermeable layer is disposed on a portion of the outer surface extending from the rear end of the body of the tampon in the first configuration, the liquid-impermeable layer may extend at least 15 mm, such as at least 20 mm, such as at least 25 mm, such as at least 30 mm, such as at least 35 mm, such as at least 40 mm, or even at least 45 mm along the length of the body of the tampon as measured from the rear end of the body of the tampon. When the liquid-impermeable layer is disposed on a portion of the outer surface extending from the rear end of the body of the tampon in the first configuration, the liquid-impermeable layer may extend up to 95 mm, such as up to 90 mm, such as up to 85 mm, such as up to 80 mm, such as up to 75 mm, such as up to 70 mm, such as up to 65 mm, such as up to 60 mm, such as up to 55 mm, or even up to 50 mm along the length of the body of the tampon as measured from the rear end of the body of the tampon.

Suitably, when the liquid-impermeable layer is disposed on a portion of the outer surface of the body of the tampon in the first configuration, the liquid-impermeable layer may be disposed on a portion of the outer surface extending from the front end of the body of the tampon.

The liquid-impermeable layer may optionally be disposed on at least a portion of the inner surface of the tampon in the first configuration. For example, in the first configuration, the liquid impermeable layer may extend from the outer surface of the body of the tampon onto at least a portion of the inner surface of the tampon. The liquid-impermeable layer may extend from the outer surface of the body of the tampon onto at least a portion of the inner surface of the tampon at the front end and/or the rear end of the body of the tampon in the first configuration.

Suitably, in the first configuration the liquid-impermeable layer may extend from the outer surface of the body of the tampon onto at least a portion of the inner surface of the tampon at the front end of the body of the tampon.

When the liquid-impermeable layer extends from the outer surface of the body of the tampon onto at least a portion of the inner surface of the tampon at the front end of the body of the tampon in the first configuration, the liquid-impermeable layer may extend any suitable distance into the bore as measured from the opening of the bore at the front end of the body of the tampon. Suitably, when the liquid-impermeable layer extends from the outer surface of the body of the tampon onto at least a portion of the inner surface of the tampon at the front end of the body of the tampon in the first configuration, the liquid-impermeable layer may extend at least 5 mm, such as at least 10 mm, such as at least 15 mm, such as at least 20 mm, such as at least 25 mm, such as at least 30 mm into the bore as measured from the opening of the bore at the front end of the body of the tampon. Suitably, when the liquid-impermeable layer extends from the outer surface of the body of the tampon onto at least a portion of the inner surface of the tampon at the front end of the body of the tampon in the first configuration, the fluid-impermeable layer may extend up to 70 mm, such as up to 60 mm, such as up to 50 mm, such as up to 40 mm, or even up to 35 mm into the bore as measured from the opening of the bore at the front end of the body of the tampon.

Suitably, when the liquid-impermeable layer extends from the outer surface of the body of the tampon onto at least a portion of the inner surface of the tampon at the front end of the body of the tampon in the first configuration, the liquid-impermeable layer may extend from 5 to 20 mm into the bore as measured from the opening of the bore at the front end of the body of the tampon.

When the liquid-impermeable layer extends from the outer surface of the body of the tampon onto at least a portion of the inner surface of the tampon at the rear end of the body of the tampon in the first configuration, the fluid impermeable layer may extend any suitable distance into the bore as measured from the opening of the bore at the rear end of the body of the tampon. Suitably, when the liquid-impermeable layer extends from the outer surface of the body of the tampon onto at least a portion of the inner surface of the tampon at the rear end of the body of the tampon in the first configuration, the liquid-impermeable layer may extend at least 5 mm, such as at least 10 mm, such as at least 15 mm, such as at least 20 mm, such as at least 25 mm, such as at least 30 mm into the bore as measured from the opening of the bore at the rear end of the body of the tampon. Suitably, when the liquid-impermeable layer extends from the outer surface of the body of the tampon onto at least a portion of the inner surface of the tampon at the rear end of the body of the tampon in the first configuration, the liquid-impermeable layer may extend up to 70 mm, such as up to 60 mm, such as up to 50 mm, such as up to 40 mm, or even up to 35 mm into the bore as measured from the opening of the bore at the rear end of the body of the tampon.

Suitably, when the liquid-impermeable layer extends from the outer surface of the body of the tampon onto at least a portion of the inner surface of the tampon at the rear end of the body of the tampon in the first configuration, the liquid-impermeable layer may extend from 5 to 20 mm into the bore as measured from the opening of the bore at the rear end of the body of the tampon.

The liquid-impermeable layer comprises a liquid-impermeable elastic material. By "elastic", and like terms as used herein, is meant that the liquid-impermeable layer is able to stretch in at least one direction, such as axially and/or laterally, and is not intended to mean that the liquid-impermeable layer must be able to return to its original shape once stretched. However, this does not exclude the possibility that the liquid-impermeable layer may return to its original shape once stretched.

The liquid-impermeable elastic material may have any suitable elasticity. Suitably, the liquid-impermeable elastic material may have an elasticity that is sufficient to allow the liquid-absorbing material of the body to expand outwards, i.e. laterally, upon absorption and/or retention of bodily fluid, such as menstrual fluid. Suitably, therefore, the liquid-impermeable elastic material may have elasticity in the lateral direction. Suitably, the liquid-impermeable elastic material may have substantially no elasticity in the axial direction such that, when the liquid-impermeable layer is on at least a portion of the outer surface of the body of the tampon, the liquid-impermeable layer is operable to allow the body of the tampon to substantially hold its shape and/or allow the liquid-absorbing material of the body of the tampon to move axially along the longitudinal axis when a compressive force is applied to the front end and/or the rear end of the body of the tampon. Suitably, therefore, the liquid-impermeable layer may have substantially no elasticity in the axial direction.

Suitably, the liquid-impermeable elastic material may have elasticity in the lateral direction.

Suitably, the liquid-impermeable elastic material may have elasticity in the lateral direction and substantially no elasticity in the axial direction.

It will be appreciated by a person skilled in the art that the limitation(s) of the material from which the liquid-impermeable elastic material is formed and/or the methods use to manufacture the liquid-impermeable elastic material and/or the tampon may mean that a certain degree of elasticity in the axial direction may suitably be tolerated.

Suitably, therefore, the liquid-impermeable elastic material may have a degree of elasticity in the axial direction.

The liquid-impermeable elastic material may comprise any suitable liquid-impermeable elastic material. Suitable liquid-impermeable elastic materials will be known to a person skilled in the art. Suitable liquid-impermeable elastic materials include, but are not limited to, one or more of the following: polyurethane; polyethylene; polypropylene; polyethylene terephthalate; and combinations thereof.

Suitably, the liquid-impermeable elastic material may comprise polyurethane.

The liquid-impermeable elastic material may be inherently substantially impermeable to at least bodily fluids, such as menstrual fluid, and the fluid(s) of the liquid-absorbing material of the body of the tampon. Additionally and/or alternatively, the liquid-impermeable elastic material may comprise an elastic material which is post-treated in order to make said elastic material impermeable to at least bodily fluids, such as menstrual fluid, and the fluid(s) of the liquid-absorbing material of the body of the tampon, for example, by having a water-proof coating applied thereto.

The tampon has a bore extending through the body along the longitudinal axis from the front end to the rear end. The bore may extend centrally through the body of the tampon or may be offset from central. Suitably, the bore may extend substantially centrally thorough the body of the tampon. More suitably, the bore may extend centrally through the body of the tampon.

The bore may be of any suitable form. The bore may be an open bore or a substantially closed bore. For example, when the bore is an open bore, the bore may have an aperture extending through the body along the longitudinal axis from the front end to the rear end. Suitably, the bore may have a diameter of <0.1 mm. For example, when the bore is a substantially closed bore, the bore may have a diameter of ≤0.1 mm, such as from 0 to 0.1 mm. It will be appreciated by a person skilled in the art that the bore may be a substantially closed bore due to the nature of the materials that the tampon comprises. For example, when the liquid-permeable layer comprises an elastic material, the bore may be a substantially closed bore due to the liquid-absorbing material of the body of the tampon and the elasticity of the liquid-permeable layer.

Suitably, the bore may be a substantially closed bore.

When the bore is an open bore, the bore may have any suitable cross-sectional shape. For example, the bore may have a substantially circular, oval, square or hexagonal cross-sectional shape. Suitably, the bore may have a substantially circular cross-sectional shape.

When the bore is an open bore and has a substantially circular cross-sectional shape, the bore may have any suitable diameter. Suitably, when the bore is an open bore and has a substantially circular cross-sectional shape, the bore may have a diameter from 0.15 to 10 mm, such as from 0.2 to 8 mm, such as from 0.3 to 7 mm, such as from 0.4 to 6 mm, such as from 0.5 to 5 mm, such as from 0.8 to 5 mm, such as from 1 to 5 mm, such as from 1 to 4 mm, such as from 1 to 3 mm, such as from 1 to 2 mm, or even from 1.5 to 2 mm. Suitably, when the bore is an open bore and has a substantially circular cross-sectional shape, the bore may have a dimeter from 0.15 to 2 mm. It will be appreciated by a person skilled in the art that the diameter of the bore may suitably depend on the width of the body of the tampon.

The bore defines an inner surface of the body of the tampon. For the avoidance of doubt, by "inner surface", and like terms as used herein, is meant the surface on the interior of the body of the tampon up to the opening of the bore at each of the front end and rear end of the body of the tampon. The inner surface of the body of the tampon suitably abuts the outer surface of the body of the tampon at the entrance to the bore at each of the front end and back end of the body of the tampon.

The tampon comprises a liquid-permeable layer. The liquid-permeable layer may comprise any suitable material. Suitably, the liquid-permeable layer may be operable to allow bodily fluids, such as menstrual fluids, to pass through said liquid-permeable layer. Suitable materials will be well known to a person skilled in the art. For example, the liquid-permeable layer may comprise textiles, such as a cotton and/or rayon textile, plastics, such as a plastic mesh (including a stamped plastic mesh or a woven plastic mesh), such as a polyurethane mesh, a polymeric network or a combination thereof.

Suitably, the liquid-permeable layer may comprise a mesh.

Suitably, the liquid-permeable layer may comprise a polyurethane mesh.

The liquid-permeable layer may be absorbent. The liquid-permeable layer, when absorbent, may be operable to absorb at least bodily fluids, such as menstrual fluids. The liquid-permeable layer, when absorbent, may be operable to absorb and/or retain bodily fluids, such as menstrual fluid.

Suitably, the liquid-permeable layer is not absorbent.

Suitably, the liquid-permeable layer may comprise an elastic material. The liquid-permeable layer may comprise an elastic material such that it is operable to allow the liquid-absorbing material of the body of the tampon to expand during use. It will be appreciated by a person skilled in the art that the liquid-absorbing material of the tampon may expand during use due to the absorption and/or retention of bodily fluid, such as menstrual fluid.

As defined hereinabove, suitably, the liquid-permeable layer may be on at least a portion of the inner surface of the body of the in the first configuration. The liquid-permeable layer may be disposed on any suitable area of the inner surface of the tampon in the first configuration. Suitably, the liquid-permeable layer may be disposed on at least 50%, such as at least 60%, such as at least 70%, such as at least 80%, such as at least 90%, or even 100% of the area of the inner surface of the body of the tampon in the first configuration.

Suitably, the liquid-permeable layer may be disposed on at least 80% of the area of the inner surface of the body of the tampon in the first configuration.

Suitably, the liquid-permeable layer may be disposed on from 80 to 100% of the area of the inner surface of the body of the tampon in the first configuration.

When the liquid-permeable layer is disposed on at least 50% of the area of the inner surface of the tampon in the first configuration, the liquid-permeable layer may be disposed on any suitable part of the inner surface of the tampon. For example, when the liquid-permeable layer is disposed on at least 50% of the area of the inner surface of the tampon in the first configuration, the liquid-permeable layer may be disposed on at least 50% of the area of inner surface of the tampon extending from the opening of the bore at front end or from the opening of the bore at the rear end of the body of the tampon.

Suitably, when the liquid-permeable layer is disposed on at least 50% of the area of the inner surface of the tampon in the first configuration, the liquid-permeable layer may be disposed on at least 50% of the area of inner surface of the tampon extending from the opening of the bore at rear end of the body of the tampon.

Suitably, when the liquid-permeable layer is disposed on at least 80% of the area of the inner surface of the body of the tampon in the first configuration, the liquid-permeable layer may be disposed on at least 80% of the area of inner surface of the tampon extending from the opening of the bore at rear end of the tampon.

The liquid-permeable layer may optionally be disposed on at least a portion of the outer surface of the tampon in the first configuration. For example, the liquid-permeable layer may extend from the inner surface of the tampon onto at least a portion of the outer surface of the tampon in the first configuration. The liquid-permeable layer may extend from the inner surface of the tampon onto at least a portion of the outer surface of the tampon at the front end and/or the rear end of the body of the tampon in the first configuration.

Suitably, the liquid-permeable layer may extend from the inner surface of the tampon onto at least a portion of the outer surface of the tampon at the rear end of the body of the tampon in the first configuration.

When the liquid-permeable layer extends from the inner surface of the tampon onto at least a portion of the outer surface of the tampon at the rear end of the body of the tampon in the first configuration, the liquid-permeable layer may extend any suitable distance onto the outer surface as measured from the opening of the bore at the rear end of the body of the tampon. Suitably, when the liquid-permeable layer extends from the inner surface of the tampon onto at least a portion of the outer surface of the tampon at the rear end of the body of the tampon in the first configuration, the liquid-permeable layer may extend at least 5 mm, such as at least 10 mm, such as at least 15 mm, such as at least 20 mm, such as at least 25 mm, such as at least 30 mm onto the outer surface of the body of the tampon as measured from the opening of the bore at the rear end of the body of the tampon. Suitably, when the liquid-permeable layer extends from the inner surface of the tampon onto at least a portion of the outer surface of the tampon at the rear end of the body of the tampon in the first configuration, the liquid-permeable layer may extend up to 70 mm, such as up to 60 mm, such as up to 50 mm, such as up to 40 mm, or even up to 35 mm onto the outer surface of the body of the tampon as measured from the opening of the bore at the rear end of the body of the tampon.

Suitably, when the liquid-permeable layer extends from the inner surface of the tampon onto at least a portion of the outer surface of the body of the tampon at the rear end of the body of the tampon in the first configuration, the liquid-permeable layer may extend from 5 to 20 mm onto the outer surface of the body of the tampon as measured from the opening of the bore at the rear end of the body of the tampon.

The body comprises a liquid-absorbing material. The liquid-absorbing material is operable to absorb and/or retain bodily fluid. The liquid-absorbing material is a fluid. By "fluid", and like terms as used herein, is meant that the liquid-absorbing material is fluid in nature, i.e. continually deforms or flows under an applied shear stress and/or external force. It will be appreciated by a person skilled in the art that the liquid-absorbing material, being operable to absorb and/or retain bodily fluid and being a fluid will suitably not be a gas.

Advantageously, the fact that the tampon of the present invention comprises a body comprising a liquid-absorbing material which is a non-gas fluid means that the tampon may be substantially free from gas such as, for example, air and/or oxygen, which reduces the likelihood of a user getting an infection from bacteria, such as, for example, staphylococcal and/or streptococcal bacteria. It is a further advantage that this means that the tampons of the present invention may be used, i.e. inserted and retained in the body, for a longer period of time than would typically be expected.

The body may comprise any suitable liquid-absorbing material. Examples of suitable liquid materials include, but are not limited to: polymeric materials, such as interpenetrating polymer networks and crosslinked polymer materials; gels; hydrogels; emulsions and combinations thereof.

Suitably, the liquid-absorbing material may comprise a liquid and/or a solid. For example, the liquid-absorbing material may comprise a liquid dispersed in a solid phase, a solid dispersed in a liquid phase or combinations thereof.

The liquid-absorbing material may comprise any suitable amount of liquid. The liquid-absorbing material may comprise at least 50 wt %, such as at least 60 wt %, such as at least 70 wt %, such as at least 80 wt %, such as at least 90 wt % liquid based on the total weight of the liquid-absorbing material.

The liquid-absorbing material may comprise water. The liquid-absorbing material may comprise any suitable amount of water. The liquid-absorbing material may comprise at least 50 wt %, such as at least 60 wt %, such as at least 70 wt %, such as at least 80 wt %, such as at least 90 wt % water based on the total weight of the liquid-absorbing material.

Suitably, the liquid-absorbing material may comprise a gel. More suitably, the liquid-absorbing material may comprise a hydrogel. Suitable hydrogels will be well known to a person skilled in the art.

It will be appreciated by a person skilled in the art that menstrual fluid typically has a salt content of up to 0.9%. Suitably, the hydrogel may be operable to absorb and/or retain a saline solution, such as a 0.9% saline solution, for example.

Suitably, the hydrogel may be biocompatible.

The liquid-absorbing material is operable to absorb and/or retain bodily fluid. The liquid-absorbing material may be operable to absorb and/or retain any suitable bodily fluid. For example, the liquid-absorbing material may be operable to absorb and/or retain menstrual fluid, blood or secretions. Suitably, the liquid-absorbing material may be operable to absorb and/or retain menstrual fluid.

The liquid-absorbing material may be a hydrogel operable to absorb and/or retain bodily fluid. The liquid-absorbing material may be a hydrogel operable to absorb and/or retain any suitable bodily fluid. For example, the liquid-absorbing material may be a hydrogel operable to absorb and/or retain menstrual fluid, blood or secretions. Suitably, the liquid-absorbing material may be a hydrogel operable to absorb and/or retain menstrual fluid.

The liquid-absorbing material may be operable to absorb and/or retain any suitable amount of bodily fluid, such as menstrual fluid. Suitably, when the bodily fluid is menstrual fluid, the liquid-absorbing material may be operable to absorb and/or retain sufficient menstrual fluid such that the tampon may be used for a time period of at least 1 hour, such as at least 2 hours, such as at least 3 hours, such as at least 4 hours, such as at least 5 hours, such as at least 6 hours, such as at least 8 hours, or even at least 9 hours.

The tampon may optionally further comprise an insertion sleeve.

The insertion sleeve may be positioned over a portion of the outer surface and/or a portion of the inner surface of the body of the tampon.

Suitably, the insertion sleeve, when present, may be positioned over at least a portion of the outer surface of the body of the tampon in the first configuration.

Suitably, the insertion sleeve, when present, may be positioned over at least a portion of the inner surface of the body of the tampon in the second configuration.

Suitably, therefore, the insertion sleeve, when present, may be operable to move between a first configuration and a second configuration.

The insertion sleeve, when present, may be positioned over the same portion of the outer surface of the body of the tampon as the layer on the outer surface of the body of the tampon in the first configuration or may be positioned over a different portion of the outer surface of the body of the tampon as the layer on the outer surface of the body of the tampon in the first configuration.

Suitably, the insertion sleeve, when present, may be positioned over substantially the same portion of the outer surface of the body of the tampon as the layer on the outer surface of the body of the tampon in the first configuration.

Suitably, when the liquid-impermeable layer is on at least a portion of the outer surface of the body of the tampon in the first configuration, the insertion sleeve, when present, may be positioned over at least some of the same portion of the outer surface of the body of the tampon as the liquid-impermeable layer.

Suitably, the insertion sleeve, when present, may be positioned over at least a portion of the front end of the body of the tampon in the first configuration. Suitably, therefore, the insertion sleeve, when present, may be substantially the same shape as the portion of the front end of the body over which said insertion sleeve, when present, is positioned in the first configuration.

Suitably, the insertion sleeve, when present may comprise a portion that extends into the bore of the tampon such that said portion of the insertion sleeve is disposed on at least a portion of the inner surface of the tampon in the first configuration. More suitably, the insertion sleeve, when present may comprise a portion that extends into the bore of the tampon at the front end of the body such that said portion of the insertion sleeve is disposed on at least a portion of the inner surface of the tampon in the first configuration. Suitably, when the insertion sleeve has a portion that is disposed on at least a portion of the inner surface of the tampon in the first configuration, the portion that it disposed on at least a portion of the inner surface of the tampon may extend any suitable distance into the bore as measured from the opening of the bore at the front end of the body of the tampon. Suitable distances are as defined hereinabove in relation to the liquid-impermeable layer. Suitably, the portion of the insertion sleeve that is disposed on at least a portion of the inner surface of the tampon may extend substantially the same distance into the bore as measured from the opening of the bore at the front end of the body as the fluid-impermeable layer.

The insertion sleeve, when present, may comprise any suitable material. Suitably, the insertion sleeve, when present, may comprise an elastic material. Suitably, the insertion sleeve, when present, may comprise a liquid-impermeable material. Suitably, the insertion sleeve, when present, may comprise a liquid-impermeable elastic material. Suitable liquid-impermeable materials are as defined hereinabove in relation to the liquid-impermeable layer.

The insertion sleeve, when present, may comprise the same material as the liquid-impermeable layer of the tampon or may comprise a different material to the liquid-impermeable layer of the tampon. Suitably, the insertion sleeve, when present, may comprise a different material to the liquid-impermeable layer.

The insertion sleeve, when present, may have any suitable elasticity. Suitably, the insertion sleeve, when present, may have substantially no elasticity in the axial direction such that the insertion sleeve, when present, is operable to allow the body of the tampon to substantially hold its shape and/or allow the liquid-absorbing material of the body of the tampon to move axially along the longitudinal axis when a compressive force is applied to the front end and/or the rear end of the body of the tampon. Suitably, therefore, the insertion sleeve, when present, may have substantially no elasticity in the axial direction.

It will be appreciated by a person skilled in the art that the limitation(s) of the material from which the insertion sleeve is formed and/or the methods used to manufacture the insertion sleeve and/or the tampon may mean that a certain degree of elasticity in the axial direction may suitably be tolerated.

Suitably, therefore, the insertion sleeve, when present, may have a degree of elasticity in the axial direction.

The insertion sleeve, when present, may have the same elasticity as the liquid-impermeable layer of the tampon or may have a different elasticity as the liquid-impermeable layer of the tampon.

Suitably, the insertion sleeve, when present, may have a different elasticity to the liquid-impermeable layer of the tampon.

Suitably, when an insertion sleeve is present, the liquid-impermeable layer of the tampon may be elastic in both the lateral and axial directions. It is an advantage that the use of an insertion sleeve may provide sufficient inelasticity in the axial direction to allow the body of the tampon to substantially hold its shape.

Advantageously, the use of an insertion sleeve enables the distance to which the tampon is self-inserted to be controlled. For example, when the liquid-impermeable layer is disposed on substantially all of the outer surface of the body of the tampon in the first configuration, the insertion sleeve may be positioned on a portion of the outer surface of the body of the tampon in the first configuration such that, in use, the insertion sleeve may be operable to apply a compressive force to either the front end and/or the rear end of the body of the tampon. It is a further advantage that the insertion sleeve enables the distance to which the tampon is 'self-inserted' to be controlled because the axial length of the insertion sleeve may substantially determine the insertion distance.

Suitably, when the liquid-absorbing material of the body of the tampon is caused to move axially along the longitudinal axis, the insertion sleeve may be caused to move inwards into the bore such that said insertion sleeve becomes located on at least a portion of the inner surface of the body of the tampon. It is an advantage that in moving inwards into the bore the insertion sleeve does not impede extraction. Without being bound by theory, this may be because the insertion sleeve does not apply a compressive force to the front end and/or rear end of the body of the tampon. It is a further advantage that in moving inwards into the bore the insertion sleeve substantially contains any initial contamination from before and/or during insertion with the core of the body of the tampon.

The tampon may further optionally comprise a rear end sleeve.

The rear end sleeve, when present, may be positioned over a portion of the outer surface and/or a portion of the inner surface of the body of the tampon, suitably at the rear end thereof.

Suitably, the rear end sleeve, when present, may be positioned over at least a portion of the outer surface of the body of the tampon in the first configuration, suitably at the rear end thereof.

Suitably, the insertion sleeve, when present, may be positioned over at least a portion of the inner surface of the body of the tampon in the second configuration.

Suitably, therefore, the insertion sleeve, when present, may be operable to move between a first configuration and a second configuration.

Suitably, the rear end sleeve, when present, may be positioned over at least a portion of the rear end of the body of the tampon in the first configuration. Suitably, therefore, the rear end sleeve, when present, may be substantially the same shape as the portion of the rear end of the body over which said rear end sleeve, when present, is positioned in the first configuration.

Suitably, the rear end sleeve, when present, may be operable to substantially prevent axial movement of the liquid-absorbing material along the longitudinal axis in the direction extending from the front end to the rear end when a compressive force is applied to the front end of the body of the tampon. Advantageously, the fact that the rear end sleeve, when present, may substantially prevent axial movement of the liquid-absorbing material along the longitudinal axis in the direction extending from the front end to the rear end when a compressive force is applied to the front end of the body of the tampon, means that the tampon may be caused to 'self-insert' in the right direction.

Suitably, the rear end sleeve, when present, may be operable to substantially seal the rear end of the body. More suitably, the rear end sleeve, when present, may be operable to substantially seal the bore at the rear end of the body. Advantageously, the fact that rear end sleeve, when present, may be operable to substantially seal the rear end of the body, more suitably to seal the bore at the rear end of the body, means, for example, that, in use, any bodily fluid, such as menstrual fluid, is substantially prevented from passing through the bore of the body of the tampon. For the avoidance of doubt, by "substantially seal the bore" in reference to the rear end sleeve suitably is when the tampon is in the first configuration.

The rear end sleeve, when present, may comprise any suitable material. Suitably, the rear end sleeve, when present, may comprise an elastic material. Suitably, the rear end sleeve, when present, may comprise a liquid-impermeable material. Suitably, the rear end sleeve, when present, may comprise a liquid-impermeable elastic material. Suitable liquid-impermeable materials are as defined hereinabove in relation to the liquid-impermeable layer.

The rear end sleeve, when present, may comprise the same material as the liquid-impermeable layer of the tampon or may comprise a different material to the liquid-impermeable layer of the tampon. Suitably, the rear end sleeve, when present, may comprise a different material to the liquid-impermeable layer.

The rear end sleeve, when present, may have the same elasticity as the liquid-impermeable layer of the tampon or may have a different elasticity to the liquid-impermeable layer of the tampon.

Suitably, the rear end sleeve, when present, may have a different elasticity to the liquid-impermeable layer of the tampon.

The rear end sleeve, when present, may have the same elasticity as the insertion sleeve, when present, or may have a different elasticity to the insertion sleeve, when present. Suitably, the rear end sleeve, when present, may have the same elasticity as the insertion sleeve, when present.

The rear end sleeve, when present, may be attached to any suitable part of the tampon. For example, the rear end sleeve, when present, may be attached to the liquid-impermeable layer and/or to the insertion sleeve, when present. Suitably, the rear end sleeve, when present, may be attached to the liquid-impermeable layer and to the insertion sleeve, when present. The rear end sleeve, when attached to the insertion sleeve, may be attached to any suitable portion of the insertion sleeve. Suitably, when the rear end sleeve is attached to the insertion sleeve, the rear end sleeve may be attached to the insertion sleeve at the junction of said rear end sleeve and said insertion sleeve.

Suitably, the tampon may comprise an insertion sleeve and a rear end sleeve.

The tampon may further optionally comprise a withdrawal element. Suitably, the withdrawal element, when present, may be operable to remove the tampon from inside the body, such as from inside the vagina. The withdrawal element may be in any suitable form. For example, the withdrawal element may comprise a string, such as a cotton and/or rayon string.

The withdrawal element may be attached to any suitable part of the tampon. For example, the withdrawal element may be attached to the rear end of the body of the tampon or may be attached to the rear end sleeve, when present. Suitably, the withdrawal element may be attached to the rear end sleeve, when present.

The tampon may further optionally comprise a front end sealing element.

The front end sealing element, when present, may be positioned over a portion of the outer surface and/or a portion of the inner surface of the body of the tampon, suitably at the front end thereof.

Suitably, the front end sealing element, when present, may be positioned over at least a portion of the outer surface of the body of the tampon in the first configuration, suitably at the front end thereof.

Suitably, the front end sealing element, when present, may be positioned over at least a portion of the inner surface of the body of the tampon in the second configuration.

Suitably, therefore, the front end sealing element, when present, may be operable to move between a first configuration and a second configuration.

Suitably, the front end sealing element may be positioned at the front end of the body of the tampon in the first configuration. The front end sealing element, when present, may be operable to substantially seal the front end of the body. More suitably, the front end sealing element, when present, may be operable to substantially seal the bore at the front end of the body. Advantageously, the fact that front end sealing element, when present, may be operable to substantially seal the front end of the body, more suitably to seal the bore at the front end of the body, means, for example, that the liquid-absorbing material of the body of the tampon is substantially prevented from becoming dehydrated, such as by evaporation, prior to use and/or substantially prevents contamination within the bore of the tampon prior to use. For the avoidance of doubt, by "substantially seal the bore" in reference to the front end sealing element suitably is when the tampon is in the first configuration.

Suitably, the front end sealing element may be operable to be broken upon the application of a compressive force to the front end and/or rear end of the body of the tampon, suitably upon the application of a compressive force to the rear end of the body of the tampon. Suitably, therefore, the front end sealing element may comprise a breakable material.

Advantageously, the use of a front end sealing element substantially prevents unintended forward movement of the tampon before it is in the correct position for insertion, such as for example 'self-insertion'.

The tampon may further optionally comprise an extraction sealing element. The extraction sealing element, when present, may be operable to substantially seal the bore at the front end of the body of the tampon after use. Advantageously, the fact that the extraction sealing element, when present, may be operable to substantially seal the bore at the front end of the body of the tampon after use, means that the tampon may be more hygienically handled than would typically be expected. For example, the absorbed and/or retained bodily fluid, such as menstrual fluid may be substantially sealed within the tampon upon removal of the tampon.

The extraction sealing element, when present, may be attached to any suitable part of the tampon. Suitably, the extraction sealing element, when present, may be attached to the front end of the body of the tampon, for example, on the fluid-impermeable layer in the first configuration.

Suitably, the extraction sealing element, when present, may be substantially covered by the insertion sleeve, when present, in the first configuration.

Suitably, the extraction sealing element, when present, may become exposed upon removal of the tampon from an opening in the body, such as from the vagina. Suitably, therefore, the extraction sealing element, when present, may become exposed in the second configuration.

The extraction sealing element, when present, may comprise an extraction loop. The extraction loop, when present, may be operable to allow extraction of the tampon by a pulling force. For example, the extraction loop, when present, may be pulled by a user either directly and/or indirectly such that the tampon may be removed by said pulling force.

The tampon may optionally comprise one or more transparent portion(s) on one or more element(s) of the tampon. Suitably, the transparent portion(s), when present, may be operable to allow a user to observe the absorbed and/or retained bodily fluid, such as menstrual fluid, after use. Advantageously, this could be used in diagnostics and/or other medical examinations, for example.

Any suitable element of the tampon may comprise one or more transparent portion(s). For example, the liquid-impermeable layer, liquid-permeable layer, insertion sleeve, when present, and/or rear end sleeve, when present, may comprise one or more transparent portion(s). For example, the liquid-impermeable layer, liquid-permeable layer, insertion sleeve, when present, and/or rear end sleeve, when present, may comprise a transparent material.

According to a third aspect of the present invention there is provided the use of a tampon according to the first aspect of the present invention for absorbing and/or retaining bodily fluid.

According to a fourth aspect of the present invention there is provided the use of a tampon according to the first aspect of the present invention for absorbing and/or retaining menstrual fluid.

According to a fifth aspect of the present invention there is provided a tampon, the tampon comprising:
  a body having a longitudinal axis, a front end, a rear end and an outer surface, said body comprising a liquid-absorbing material operable to absorb and/or retain bodily fluid;
  a bore extending through the body along the longitudinal axis from the front end to the rear end, said bore defining an inner surface;
  a liquid-impermeable layer, said liquid-impermeable layer comprising a liquid-impermeable elastic material; and
  a liquid-permeable layer;
  wherein the liquid-absorbing material is a fluid;
  wherein one of the liquid-impermeable layer or the liquid-permeable layer is on at least a portion of the outer surface of the body of the tampon and the other of the liquid-impermeable layer or the liquid-permeable layer is on at least a portion of the inner surface of the body;
and wherein the liquid-impermeable layer and the liquid-permeable layers together form a reversible sleeve.

According to a sixth aspect the present invention there is provided a tampon, the tampon comprising:
  a body having a longitudinal axis, a front end, a rear end and an outer surface, said body comprising a liquid-absorbing material operable to absorb and/or retain bodily fluid;
  a bore extending through the body along the longitudinal axis from the front end to the rear end, said bore defining an inner surface;
  a liquid-impermeable layer, said liquid-impermeable layer comprising a liquid-impermeable elastic material; and
  a liquid-permeable layer;
  wherein the liquid-absorbing material is a fluid;
  wherein the liquid-impermeable layer is on at least a portion of the outer surface of the body of the tampon and the liquid-permeable layer is on at least a portion of the inner surface of the body;
  and wherein, in use, the liquid-impermeable layer and the liquid-permeable layers are operable to move between a first configuration and a second configuration.

According to a seventh aspect of the present invention there is provided a tampon, the tampon comprising:
  a body having a longitudinal axis, a front end, a rear end and an outer surface, said body comprising a liquid-absorbing material operable to absorb and/or retain bodily fluid;
  a bore extending through the body along the longitudinal axis from the front end to the rear end, said bore defining an inner surface;
  a liquid-impermeable layer, said liquid-impermeable layer comprising a liquid-impermeable elastic material; and
  a liquid-permeable layer;
  wherein the liquid-absorbing material is a fluid;
  wherein the liquid-permeable layer is on at least a portion of the outer surface of the body of the tampon and the liquid-impermeable layer is on at least a portion of the inner surface of the body;
and wherein, in use, the liquid-impermeable layer and the liquid-permeable layers are operable to move between a first configuration and a second configuration.

According to an eighth aspect of the present invention there is provided a tampon, the tampon comprising:
  a body having a longitudinal axis, a front end, a rear end and an outer surface, said body comprising a liquid-absorbing material operable to absorb and/or retain bodily fluid;
  a bore extending through the body along the longitudinal axis from the front end to the rear end, said bore defining an inner surface;
  a liquid-impermeable layer, said liquid-impermeable layer comprising a liquid-impermeable elastic material; and
  a liquid-permeable layer;
  wherein the liquid-absorbing material is a fluid;
  wherein the liquid-impermeable layer is on at least a portion of the outer surface of the body of the tampon and the liquid-permeable layer is on at least a portion of the inner surface of the body;
  and wherein the liquid-impermeable layer and the liquid-permeable layers together form a reversible sleeve.

According to a ninth aspect of the present invention there is provided a tampon, the tampon comprising:
  a body having a longitudinal axis, a front end, a rear end and an outer surface, said body comprising a liquid-absorbing material operable to absorb and/or retain bodily fluid;
  a bore extending through the body along the longitudinal axis from the front end to the rear end, said bore defining an inner surface;
  a liquid-impermeable layer, said liquid-impermeable layer comprising a liquid-impermeable elastic material; and
  a liquid-permeable layer;
  wherein the liquid-absorbing material is a fluid;
  wherein the liquid-permeable layer is on at least a portion of the outer surface of the body of the tampon and the liquid-impermeable layer is on at least a portion of the inner surface of the body;

and wherein the liquid-impermeable layer and the liquid-permeable layers together form a reversible sleeve.

Suitable features of the third, fourth, fifth, sixth, seventh, eighth and/or ninth aspects of the present invention are as defined in relation to the first and/or second aspects of the present invention.

All of the features contained herein may be combined with any of the above aspects and in any combination.

BRIEF DESCRIPTION OF DRAWINGS

For a better understanding of the invention, and to show how embodiments of the same may be carried into effect, reference will now be made, by way of example only, to the accompanying drawings, in which.

DETAILED DESCRIPTION

Figure 1:
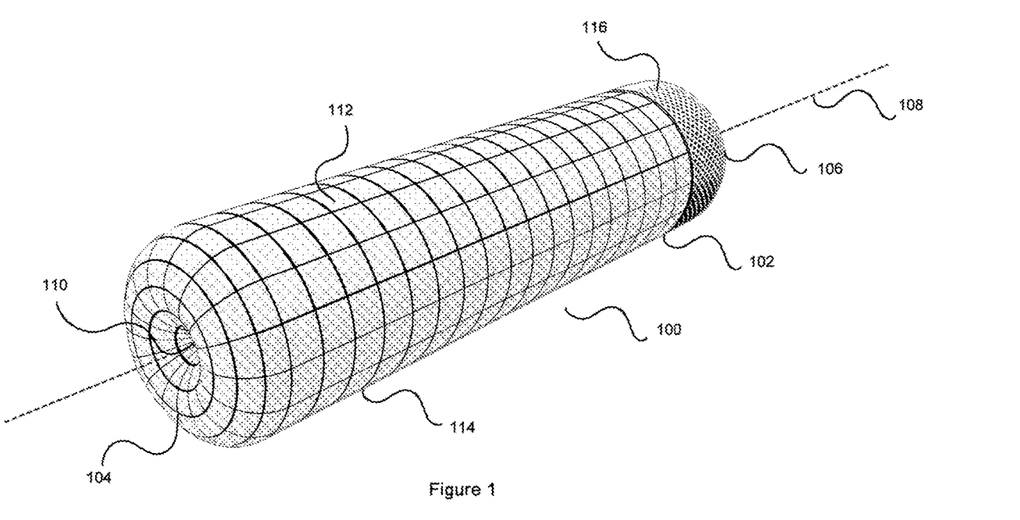
FIG. 1 shows a perspective view of a tampon according to an exemplary embodiment of the present invention.

FIG. 1 shows a tampon (100) according to the present invention prior to insertion into the vagina. The tampon (100) has a cylindrical body (102) having a length of 57 mm and a width (diameter) of 14 mm. The body (102) of the tampon (100) has a front end (104), a rear end (106) and a longitudinal axis (108) running centrally along the length of the body (102) of the tampon (100). The front end (104) and the rear end (106) of the body (102) are both dome shaped. The curved portion of the front end (104) is 3.5 mm as measured from the front end (104) of the body (102) of the tampon (100). The curved portion of the rear end (106) is 3.5 mm as measured from the rear end (106) of the body (102) of the tampon (100). The body (102) has a bore (110) extending through the body (102) along the longitudinal axis (108) defining an inner surface (not shown). The bore (110) is a closed bore and therefore has a diameter of 0.1 mm. The body (102) has an outer surface (112) which has thereon a liquid-impermeable layer (114) formed from polyurethane. The liquid impermeable layer (114) is disposed on the outer surface (112) of the body (102) from the opening of the bore (110) at the front end (104) of the body (102) to a distance of 48.5 mm along the length of the body (102). In other words, 48.5 mm of the body (102) of the tampon (100) extending from the opening of the bore (110) at the front end (104) has the liquid-impermeable layer (114) disposed thereon.

The tampon has liquid-permeable layer (116) formed from a polyurethane mesh. The liquid-permeable layer (116) is disposed on the inner surface (not shown) of the body (102). The liquid-permeable layer (116) extends onto the outer surface (112) of the body (102) of the tampon (100) from the opening of the bore (110) at the rear end (106) of the body (102) to a distance of 8.5 mm along the length of the body (102). In other words, 8.5 mm of the outer surface (112) of the body (102) of the tampon (100) extending from the opening of the bore (110) at the rear end (106) has the liquid-permeable layer (116) disposed thereon.

The liquid-impermeable layer (114) and liquid-permeable layer (116) together form a reversible sleeve.

The body (102) is formed from a hydrogel (not shown). The hydrogel (not shown) is operable to absorb and/or retain menstrual fluid.

The tampon (100) is operable to 'self insert' into the body, such as into the vagina, upon the application of a compressive force to the rear end (106) of the body (102) of the tampon (100). Upon the application of a compressive force to the rear end (106) of the body (102) of the tampon (100), the hydrogel (not shown) is caused to move in an axial direction along the longitudinal axis (108) in the direction running from the rear end (106) to the front end (104) of the body (102) of the tampon (100), as will be described in more detail in FIGS. 4 and 5.

Figure 2:
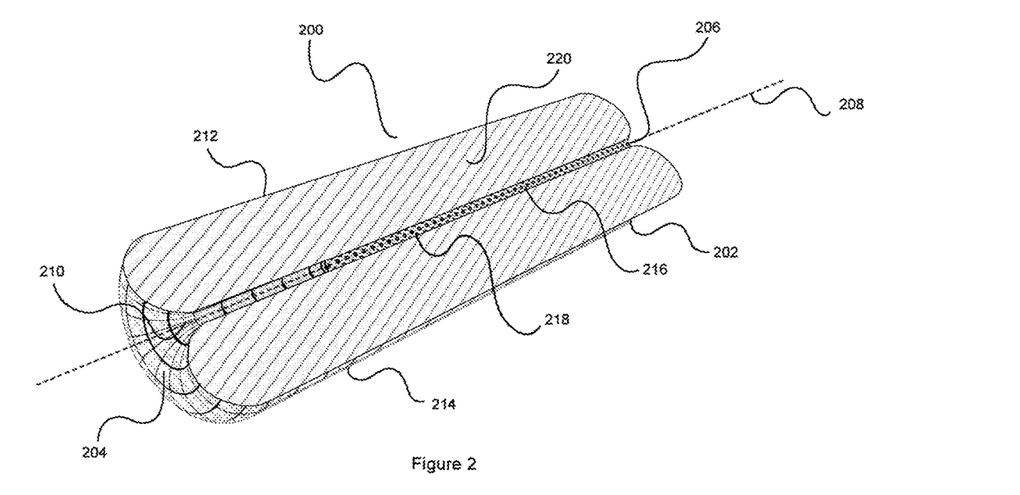
FIG. 2 shows a sectional view of a tampon according to another exemplary embodiment of the present invention.

FIG. 2 shows another tampon (200) according to the present invention in sectional view. The tampon (200) is shown prior to insertion into the vagina. The tampon (200) has a cylindrical body (202) having a length of 57 mm and a width (diameter) of 14 mm. The body (202) of the tampon (200) has a front end (204), a rear end (206) and a longitudinal axis (208) running centrally along the length of the body (202) of the tampon (200). The front end (204) and the rear end (206) of the body (202) are both dome shaped. The curved portion of the front end (204) is 3.5 mm as measured from the front end (204) of the body (202) of the tampon (200). The curved portion of the rear end (206) is 3.5 mm as measured from the rear end (206) of the body (202) of the tampon (200). The body (202) has a bore (210) extending through the body (202) along the longitudinal axis (208) defining an inner surface (218). The bore (210) is a closed bore and therefore has a diameter of 0.1 mm. The body (202) has an outer surface (212) which has thereon a liquid-impermeable layer (214) formed from polyurethane. The liquid-impermeable layer (214) is disposed on the outer surface (212) of the body (202) from the opening of the bore (210) at the front end (204) of the body (202) to a distance of 48.5 mm along the length of the body (202). In other words, 48.5 mm of the body (202) of the tampon (200) extending from the opening of the bore (210) at the front end (204) has the liquid-impermeable layer (214) disposed thereon. The liquid-impermeable layer (214) extends into the bore (210) and is disposed on the inner surface (218) of the body (202) of the tampon (200), for a distance of 13.5 mm extending from the opening of the bore (210) at the front end (204) of the body (202) of the tampon (200).

The tampon has liquid-permeable layer (216) formed from a polyurethane mesh. The liquid-permeable layer (216) is disposed on the inner surface (218) of the body (202). The liquid-permeable layer (216) extends into the inner surface (218) of the tampon (200) from the opening of the bore (210) at the rear end (206) of the body (202) to a distance of 40 mm along the length of the bore (210). In other words, 40 mm of the inner surface (212) of the tampon (200) extending from the opening of the bore (210) at the rear end (206) has the liquid-permeable layer (216) disposed thereon.

The liquid-permeable layer (216) extends onto the outer surface (212) of the body (202) of the tampon (200) from the opening of the bore (210) at the rear end (206) of the body (202) to a distance of 8.5 mm along the length of the body (202). In other words, 8.5 mm of the outer surface (212) of the body (202) of the tampon (200) extending from the opening of the bore (210) at the rear end (206) has the liquid-permeable layer (216) disposed thereon.

The liquid-impermeable layer (214) and liquid-permeable layer (216) together form a reversible sleeve.

The body (202) is formed from a hydrogel (220). The hydrogel (220) is operable to absorb and/or retain menstrual fluid.

The tampon (200) is operable to 'self insert' into the body, such as into the vagina, upon the application of a compressive force to the rear end (206) of the body (202) of the tampon (200). Upon the application of a compressive force to the rear end (206) of the body (202) of the tampon (200), the hydrogel (not shown) is caused to move in an axial direction along the longitudinal axis (208) in the direction running from the rear end (206) to the front end (204) of the body (202) of the tampon (200), as will be described in more detail in FIGS. 4 and 5.

Figure 3:
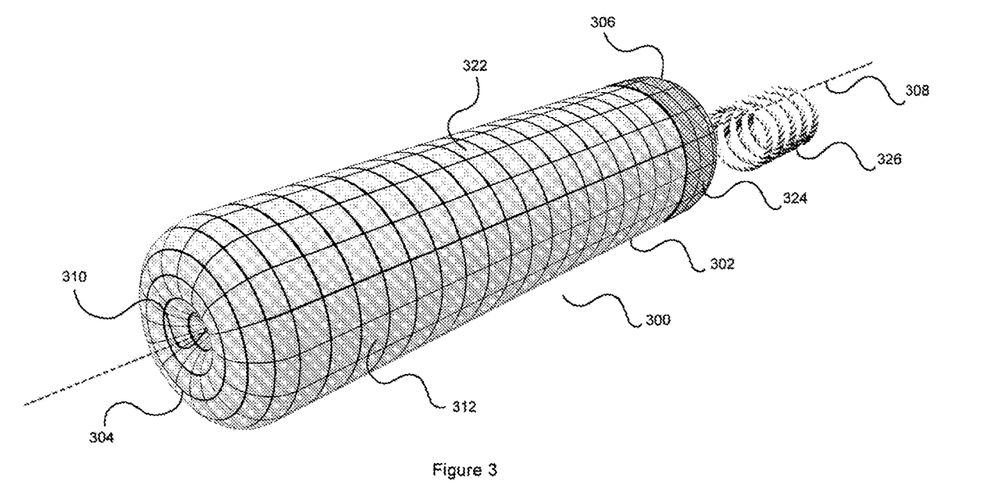
FIG. 3 shows a perspective view of a tampon according to another exemplary embodiment of the present invention.

FIG. 3 shows another tampon (300) according to the present invention prior to insertion into the vagina. The tampon (300) has a cylindrical body (302) having a length of 57 mm and a width (diameter) of 14 mm. The body (302) of the tampon (300) has a front end (304), a rear end (306) and a longitudinal axis (308) running centrally along the length of the body (302) of the tampon (300). The front end (304) and the rear end (306) of the body (302) are both dome shaped. The curved portion of the front end (304) is 3.5 mm as measured from the front end (304) of the body (302) of the tampon (300). The curved portion of the rear end (306) is 3.5 mm as measured from the rear end (306) of the body (302) of the tampon (300). The body (302) has a bore (310) extending through the body (302) along the longitudinal axis (308) defining an inner surface (not shown). The bore (310) is a closed bore and therefore has a diameter of 0.1 mm. The body (302) has an outer surface (312) which has thereon a liquid-impermeable layer (not shown) formed from polyurethane. The liquid-impermeable layer (not shown) is disposed on the outer surface (312) of the body (302) from the opening of the bore (310) at the front end (304) of the body (302) to a distance of 48.5 mm along the length of the body (302). In other words, 48.5 mm of the body (302) of the tampon (300) extending from the opening of the bore (310) at the front end (304) has the liquid-impermeable layer (not shown) disposed thereon.

The tampon has liquid-permeable layer (not shown) formed from a polyurethane mesh. The liquid-permeable layer (not shown) is disposed on the inner surface (not shown) of the body (302). The liquid-permeable layer (not shown) extends onto the outer surface (312) of the body (302) of the tampon (300) from the opening of the bore (310) at the rear end (306) of the body (302) to a distance of 8.5 mm along the length of the body (302). In other words, 8.5 mm of the outer surface (312) of the body (302) of the tampon (300) extending from the opening of the bore (310) at the rear end (306) has the liquid-permeable layer (316) disposed thereon.

The liquid-impermeable layer (not shown) and liquid-permeable layer (not shown) together form a reversible sleeve.

The body (302) is formed from a hydrogel (not shown). The hydrogel (not shown) is operable to absorb and/or retain menstrual fluid.

The tampon (300) has an insertion sleeve (322) positioned over the same portion of the outer surface (312) of the body (302) of the tampon (300) as the liquid-impermeable layer (not shown). The insertion sleeve (322) is also disposed on the same portion of the inner surface (not shown) of the body (302) of the tampon (300) as the liquid-impermeable layer (not shown). The insertion sleeve (322) is made from polyurethane. The insertion sleeve (322) provides sufficient rigidity in the axial direction to enable the tampon (300) to substantially hold its shape.

The tampon (300) has a rear end sleeve (324) positioned at the rear end (306) of the body (302) of the tampon (300). The rear end sleeve (324) is positioned over the same portion of the outer surface (312) of the body (302) of the tampon (300) as the liquid-permeable layer (not shown), however, the rear end sleeve (324) does not enter the bore (310) and, therefore, is not disposed on the inner surface (not shown) of the body (302) of the tampon (300). The rear end sleeve (322) is made from polyurethane. The rear end sleeve (324) substantially seals the rear end (306) of the body (302) of the tampon (300).

The tampon (300) has a withdrawal element (326). The withdrawal element (326) is formed from a cotton/rayon string. The withdrawal element (326) is attached to the rear end sleeve (324) such that it is positioned substantially centrally at the rear end (306) of the body (302) of the tampon (300).

The tampon (300) is operable to 'self insert' into the body, such as into the vagina, upon the application of a compressive force to the rear end (306) of the body (302) of the tampon (300). Upon the application of a compressive force to the rear end (306) of the body (302) of the tampon (300), the hydrogel (not shown) is caused to move in an axial direction along the longitudinal axis (308) in the direction running from the rear end (306) to the front end (304) of the body (302) of the tampon (300), as will be described in more detail in FIGS. 4 and 5.

Figure 4:
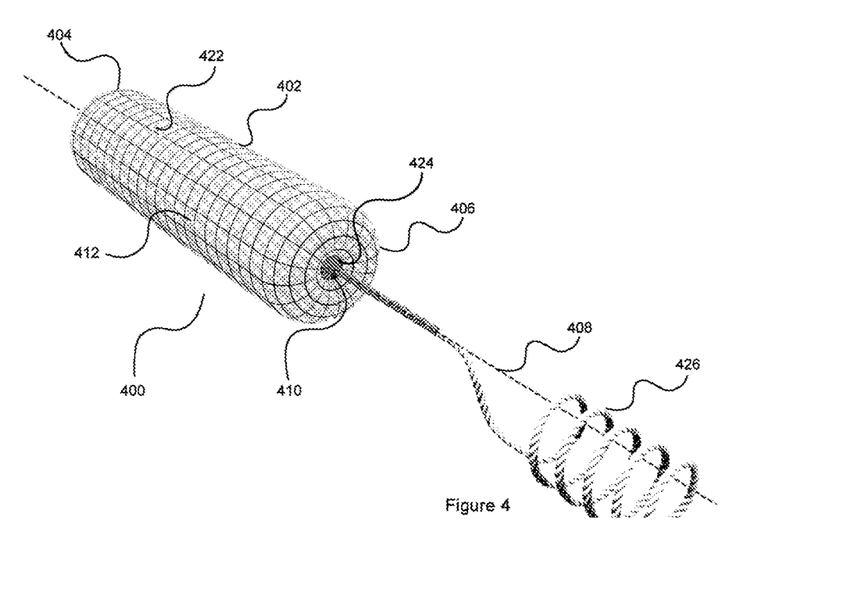
FIG. 4 shows a perspective view of a tampon according to another exemplary embodiment of the present invention as depicted when 30% inserted into the human vagina.

FIG. 4 shows another tampon (400) according to the present invention. The tampon (400) is shown when 30% inserted into the vagina. The tampon (400) has a cylindrical body (402) having a length of 57 mm and a width (diameter) of 14 mm. The body (402) of the tampon (400) has a front end (404), a rear end (406) and a longitudinal axis (408) running centrally along the length of the body (402) of the tampon (400). The front end (404) and the rear end (406) of the body (402) are both dome shaped. The curved portion of the front end (404) is 3.5 mm as measured from the front end (404) of the body (402) of the tampon (400). The curved portion of the rear end (406) is 3.5 mm as measured from the rear end (406) of the body (402) of the tampon (400). The body (402) has a bore (410) extending through the body (402) along the longitudinal axis (408) defining an inner surface (not shown). The bore (410) is a closed bore and therefore has a diameter of 0.1 mm. The body (402) has an outer surface (412) which has thereon a liquid-impermeable layer (not shown) formed from polyurethane.

The tampon has liquid-permeable layer (not shown) formed from a polyurethane mesh. The liquid-permeable layer (not shown) is disposed on the inner surface (not shown) of the body (402) of the tampon (400). The liquid-impermeable layer (not shown) and liquid-permeable layer (not shown) together form a reversible sleeve.

The body (402) is formed from a hydrogel (not shown). The hydrogel (not shown) is operable to absorb and/or retain menstrual fluid.

The tampon (400) has an insertion sleeve (422). The insertion sleeve (422) is made from polyurethane. The insertion sleeve (422) provides sufficient rigidity in the axial direction to enable the tampon (400) to substantially hold its shape.

The tampon (400) has a rear end sleeve (424) positioned at the rear end (406) of the body (402) of the tampon (400). The rear end sleeve (422) is made from polyurethane.

The tampon (400) has a withdrawal element (426). The withdrawal element (326) is formed from a cotton/rayon string. The withdrawal element (426) is attached to the rear end sleeve (424) such that it is positioned substantially centrally at the rear end (406) of the body (402) of the tampon (400).

Upon application of a compressive force to the rear end (406) of the body (402) of the tampon (400) by a user, the hydrogel (not shown) is caused to move in an axial direction along the longitudinal axis (408) in the direction running from the rear end (406) to the front end (404) of the body (402) of the tampon (400). In FIG. 4, a compressive force has been applied to the rear end (406) of the body (402) of the tampon (400) by a user such that the tampon (400) has been caused to move about 30% of the distance into the vagina (not shown) due to the aforementioned fluid movement of the hydrogel (not shown). As shown in FIG. 4, upon the application of a compressive force to the rear end (406) of the body (402) of the tampon (400) by a user, the liquid-impermeable layer (not shown) and the insertion sleeve (422) have been caused to move axially along the outer surface (412) of the body (402) of the tampon (400) and in doing so have moved towards the rear end (406) of the body (402) of the tampon (400). Upon the application of a compressive force to the rear end (406) of the body (402) of the tampon (400) by a user, the liquid-permeable layer (not shown) and the rear end sleeve (424) have been caused to towards the bore (410) at the rear end of the body (402) of the tampon (400).

When disposed at the rear end (406) of the body (402) of the tampon (400), the insertion sleeve (422) applies a compressive force to the rear end (406) of the body (402) of the tampon (400) due to the elastic nature of said insertion sleeve (422). This compressive force may cause the hydrogel (not shown) to move further axially along the longitudinal axis.

Figure 5:
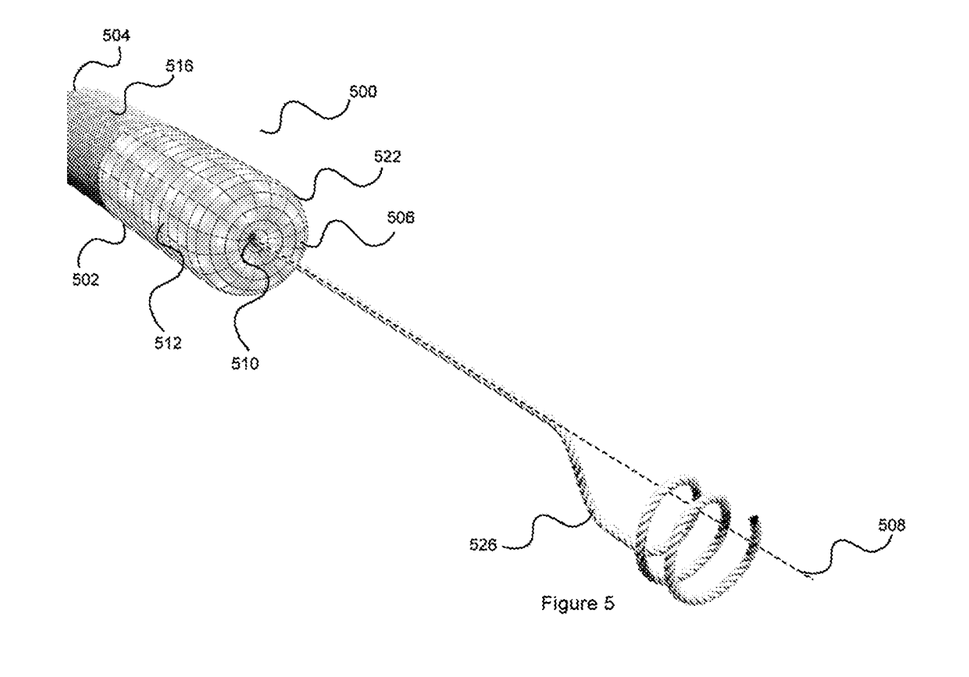
FIG. 5 shows a perspective view of a tampon according to another exemplary embodiment of the present invention as depicted when 55% inserted into the human the vagina.

FIG. 5 shows another tampon (500) according to the present invention. The tampon (500) is shown when 55% inserted into the vagina. The tampon (500) has a cylindrical body (502) having a length of 57 mm and a width (diameter) of 14 mm. The body (502) of the tampon (500) has a front end (504), a rear end (506) and a longitudinal axis (508) running centrally along the length of the body (502) of the tampon (500). The front end (504) and the rear end (506) of the body (502) are both dome shaped. The curved portion of the front end (504) is 3.5 mm as measured from the front end (504) of the body (502) of the tampon (500). The curved portion of the rear end (506) is 3.5 mm as measured from the rear end (506) of the body (502) of the tampon (500). The body (502) has a bore (510) extending through the body (502) along the longitudinal axis (508) defining an inner surface (not shown). The bore (510) is a closed bore and therefore has a diameter of 0.1 mm. The body (502) has an outer surface (512) which has thereon a liquid-impermeable layer (not shown) formed from polyurethane.

The tampon has liquid-permeable layer (516) is formed from a polyurethane mesh. The liquid-permeable layer (516) is disposed on the inner surface (not shown) of the body (502) of the tampon (500). The liquid-impermeable layer (not shown) and liquid-permeable layer (516) together form a reversible sleeve.

The body (502) is formed from a hydrogel (not shown). The hydrogel (not shown) is operable to absorb and/or retain menstrual fluid.

The tampon (500) has an insertion sleeve (522). The insertion sleeve (522) is made from polyurethane and has a higher degree of inelasticity in the axial direction compared to the liquid-impermeable layer (516). The insertion sleeve (522) provides sufficient rigidity in the axial direction to enable the tampon (500) to substantially hold its shape.

The tampon (500) has a rear end sleeve (not shown). The rear end sleeve (not shown) is made from polyurethane.

The tampon (500) has a withdrawal element (526). The withdrawal element (526) is formed from a cotton/rayon string. The withdrawal element (526) is attached to the rear end sleeve (not shown). The withdrawal element (526) has been partially pulled into the bore (510).

As shown in FIG. 5, and in comparison to the tampon (400) as shown in FIG. 4, upon the application of a compressive force to the rear end (506) of the body (502) of the tampon (500) by the insertion sleeve (522), the liquid-impermeable layer (not shown) and the insertion sleeve (522) have been caused to move further axially along the outer surface (512) of the body (502) of the tampon (500) and in doing so has moved even further towards the rear end (506) of the body (502) of the tampon (500) and into the bore (510). The liquid-impermeable layer (not shown) and the insertion sleeve (522) are therefore disposed on at least a portion of the inner surface (not shown) of the body (502) of the tampon (500) at the rear end (506). Upon the application of a compressive force to the rear end (506) of the body (502) of the tampon (500) by a user, the liquid-permeable layer (516) has been caused to move outwards from the bore (510) of the body (502) of the tampon (500) onto the outer surface (512) of the body (502) of the tampon (500) at the front end (504) and in doing so has become disposed on a portion of the outer surface (512) of the body (502) of the tampon (500) at the front end (504). The liquid-permeable layer (516) being disposed on a portion of the outer surface (512) of the body (502) of the tampon (500) at the front end (504) means that it is able to allow menstrual fluid to pass through said liquid-permeable layer (516) such that the menstrual fluid may be retained and/or absorbed by the hydrogel (not shown) of the body (502) of the tampon (500).

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:
1. A tampon, the tampon comprising:
   a body having a longitudinal axis, a front end, a rear end and an outer surface, said body comprising a liquid-absorbing material operable to absorb and/or retain bodily fluid;

a bore extending through the body along the longitudinal axis from the front end to the rear end, said bore defining an inner surface;

a liquid-impermeable layer, said liquid-impermeable layer comprising a liquid-impermeable elastic material; and a liquid-permeable layer;

wherein the liquid-absorbing material is a fluid;

wherein one of the liquid-impermeable layer or the liquid-permeable layer is on at least a portion of the outer surface of the body of the tampon and the other of the liquid-impermeable layer or the liquid-permeable layer is on at least a portion of the inner surface of the body;

and wherein, in use, the liquid-impermeable layer and the liquid-permeable layers are operable to move between a first configuration and a second configuration.

2. The tampon according to claim 1, wherein the tampon is an intravaginal tampon operable to absorb and/or retain menstrual fluid.

3. The tampon according to claim 1, wherein the tampon is operable to move forward along the longitudinal axis when a compressive force is applied to the rear end of the body.

4. The tampon according to claim 1, wherein the liquid-impermeable layer is on at least a portion of the outer surface of the body of the tampon and the liquid-permeable layer is on at least a portion of the inner surface of the body of the tampon in the first configuration.

5. The tampon according to claim 1, wherein the liquid-permeable layer is on at least a portion of the outer surface of the body of the tampon and the liquid-impermeable layer is on at least a portion of the inner surface of the body of the tampon in the second configuration.

6. The tampon according to claim 1, wherein the liquid-impermeable layer and the liquid-permeable layer together form a reversible sleeve.

7. The tampon according to claim 1, wherein the liquid-absorbing material comprises a hydrogel.

8. The tampon according to claim 1, wherein the liquid-impermeable elastic material has elasticity in a lateral direction of the liquid-impermeable elastic material and substantially no elasticity in an axial direction of the liquid-impermeable elastic material.

9. The tampon according to claim 1, wherein the bore is a closed bore.

10. The tampon according to claim 1, further comprising an insertion sleeve.

11. The tampon according to claim 1, further comprising a rear end sleeve.

12. The tampon according to claim 1, further comprising a withdrawal element.

13. The tampon according to claim 1, further comprising a front end sealing element.

14. The tampon according to claim 1, further comprising an extraction sealing element.

15. The tamp according to claim 14, wherein the extraction sealing element comprises an extraction loop.

16. The tampon according to claim 1, wherein the liquid-impermeable layer, the liquid-permeable layer, an optional insertion sleeve, and/or an optional rear end sleeve comprise one or more transparent portion(s).

17. A method of using the tampon according to claim 1, comprising inserting the tampon of claim 1 into a vagina of a user to absorb menstrual fluid.

18. A tampon, the tampon comprising:

a body having a longitudinal axis, a front end, a rear end and an outer surface, said body comprising a liquid-absorbing material operable to absorb and/or retain bodily fluid;

a bore extending through the body along the longitudinal axis from the front end to the rear end, said bore defining an inner surface;

a liquid-impermeable layer, said liquid-impermeable layer comprising a liquid-impermeable elastic material; and a liquid-permeable layer;

wherein the liquid-absorbing material is a fluid;

wherein one of the liquid-impermeable layer or the liquid-permeable layer is on at least a portion of the outer surface of the body of the tampon and the other of the liquid-impermeable layer or the liquid-permeable layer is on at least a portion of the inner surface of the body;

and wherein the liquid-impermeable layer and the liquid-permeable layers together form a reversible sleeve.

* * * * *

UNITED STATES PATENT AND TRADEMARK OFFICE
CERTIFICATE OF CORRECTION

| | |
|---|---|
| PATENT NO. | : 12,016,755 B2 |
| APPLICATION NO. | : 17/422585 |
| DATED | : June 25, 2024 |
| INVENTOR(S) | : John Anthony Bairstow |

It is certified that error appears in the above-identified patent and that said Letters Patent is hereby corrected as shown below:

In the Claims

Claim 15 Column 28 Line 13 should read:
"The tampon according to claim 14, wherein the extrac-"

Signed and Sealed this
Tenth Day of September, 2024

Katherine Kelly Vidal
*Director of the United States Patent and Trademark Office*